United States Patent

Bendicks et al.

[11] Patent Number: 5,818,600
[45] Date of Patent: Oct. 6, 1998

[54] OPTOELECTRONIC SENSOR DEVICE FOR THE DETECTION OF THE DEGREE OF WETTING OF THE TRANSPARENT SCREEN OF A MOTOR VEHICLE WITH PRECIPITATION

[76] Inventors: Norbert Bendicks, Caller Str. 73, 58675 Hemer; Berthold Esders, Eichenwald 3, 58579 Schalksmühle, both of Germany

[21] Appl. No.: 497,144

[22] Filed: Jul. 30, 1995

[30] Foreign Application Priority Data

Jul. 12, 1994 [DE] Germany .................. 44 24 454.1

[51] Int. Cl.$^6$ ................. G01N 21/88; B60S 1/02
[52] U.S. Cl. ............. 356/445; 250/227.25; 250/341.8; 318/DIG. 2
[58] Field of Search ............. 356/445; 250/227.25, 250/341.8; 318/DIG. 2

[56] References Cited

U.S. PATENT DOCUMENTS 4,701,613 10/1987 Watanabe et al. ............. 350/577
4,867,561 9/1989 Fujii et al. ............. 356/237

*Primary Examiner*—Vincent P. McGraw
*Attorney, Agent, or Firm*—Brooks & Kushman P.C.

[57] ABSTRACT

An optoelectronic sensor device for the detection of the degree of wetting of a transparent vehicle screen with precipitation, includes a beam guide with two opposing parallel surfaces and two surfaces which lie opposite to one another and which are angled in opposing fashion through which beams enter and exit, one of the parallel surfaces being coupled to the vehicle screen in an optical fashion, the beam entry surface cooperating with an optical transmitter and the exit surface cooperating with an optical receiver. The device limits the wavelength of rays which exit from the beam guide to the operating range of the beam transmitter. Two filters (4) are incorporated in the beam path whose pass ranges overlap within a narrow frequency band.

15 Claims, 4 Drawing Sheets

OPTOELECTRONIC SENSOR DEVICE FOR THE DETECTION OF THE DEGREE OF WETTING OF THE TRANSPARENT SCREEN OF A MOTOR VEHICLE WITH PRECIPITATION

TECHNICAL FIELD

The present invention concerns an optoelectronic sensor device for the detection of the degree of wetting of a transparent vehicle screen with precipitation.

BACKGROUND ART

Sensor devices of the relevant kind are provided with a beam guide which exhibits two parallel outer surfaces, one of which is attached to the windshield by means of optical adhesive or similar means. The beam guide also exhibits two surfaces which lie opposite to one another and which are angled in opposing fashion, through which the beams enter and exit. To this end, one of the surfaces cooperates with a beam transmitter and the other cooperates with a beam receiver.

One version of this type of device has been described in the patent DE-PS 33 14 770 C2. This device uses the change in the total internal reflection angle which takes place when the screen is wetted to a greater or lesser degree. As the sensitivity curve of the receiver is different from that of the transmitter, interference beams have a marked effect on the measurement result. This is particularly true of beams within the visible wavelengths.

SUMMARY OF THE INVENTION

The aim of the current invention is to limit the range of the beams exiting from the beam guide so that it conforms with the operational range of the sensor as closely as possible.

This aim is realized in that two filters are built into the beam path whose transmission range overlaps in a narrow frequency band.

The invention differs from the prior art in that the operational range of the beams entering the receiver specifically conforms to the operational range of the sensor.

This enables a high degree of sensitivity to be achieved within the operational range of the sensor with minimal interference.

The beams conform to the operational range of the sensor particularly well when the overlapping area is identical with the operational range of the beam transmitter. Interference is particularly low when the operational range is within the spectrum 650–750 microns.

Interference beams are eliminated particularly effectively when one filter is in the form of an interference filter whose transmission range basically corresponds to that of the operational range of the sensor.

If a band pass filter system is used, good results can be achieved if at least one filter is in the form of a band pass filter whose transmission range includes the operational range of the sensor with one band edge lying in the immediate neighborhood of the operational range.

Good results with two band pass filters can be achieved if the transmission range in the visible spectrum of one band pass filter borders on the operational range in the long-wave range and the transmission range in the visible spectrum of the other band pass filter borders on the operational range in the short-wave range.

An effective and economical design can be achieved if one filter is incorporated in the beam guide.

The characteristics of the beam guide can be substantially influenced, because the material of which the guide is made consists of a mixture of glass types with different characteristics.

A further effective design possibility is that of creating one filter in the form of a dielectric layer which is applied to the beam guide by means of sputtering. A further possibility is that of using the adhesive layer between the beam guide and the windscreen as a filter.

Yet another possibility is that of mounting a separate filter elements on the beam receiver holder.

Particular examples of the invention can be seen in the drawings, as follows:

BEST MODES FOR CARRYING OUT THE INVENTION

Figure 1:
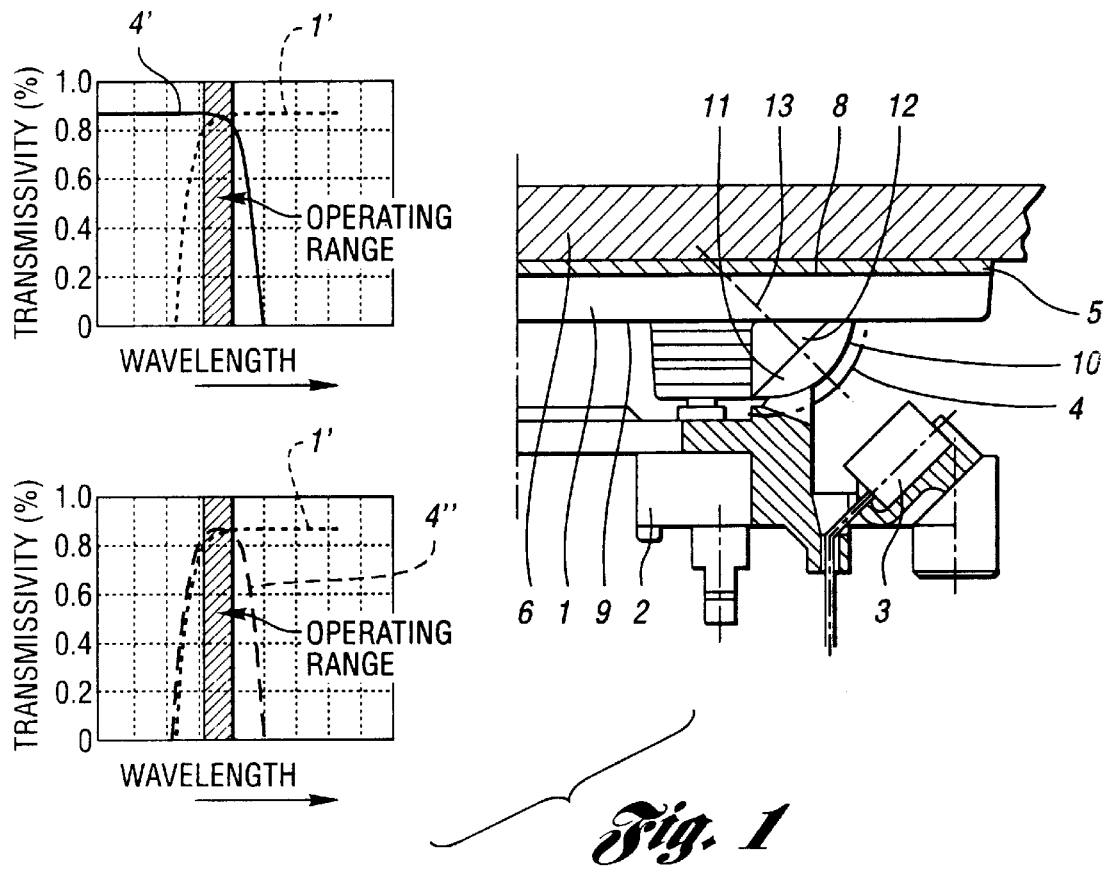
FIG. 1 is a section through the receiver area of the sensor device, together with two filter diagrams.

In FIG. 1, the receiver half of the sensor device is shown, the other half of the sensor device which is not shown can in principle be completed on the other side of the broken center line to be symmetrical with the illustrated portion. The sensor device includes a beam guide 1, which exhibits two parallel outer surfaces 8 and 9 and two surfaces, one for beam entry, not shown for the sake of simplicity, and one for beam exit 10. The beam exit surface is completed by a convergent lens 11, so that a convergent beam emerges. Convergent lens 11 and an additional support piece 12 can be manufactured in one piece with the beam guide 1 or they can consist of separate parts. The exit axis of the beam 13 is inclined to outer surface 8. It is most advantageous if the angle of inclination is 45°. At any event, the beam exit axis forms an angle of 90° with the beam entry axis (not shown).

The beam guide fits into base 2, which acts as a carrier for all the parts. An optoelectronic receiver 3, for example a photodiode, phototransistor or similar, is directed towards exit axis 13.

Beam guide 1 is attached to the vehicle screen 6 by means of a transparent coupling medium 5, for example transparent adhesive, which permits optical coupling with the screen. The vehicle screen can be a front windshield, a rear windshield or another transparent pane.

If no rain or other deposit is present, the beam of rays which is emitted by the transmitter is totally reflected within the beam guide and reaches the optoelectronic sensor 3 along the exit axis 13. The beam of rays is in a narrow band and shown in the filter graphs as a rectangular operating range. When it rains, the surface of the vehicle screen is wetted to a greater or lesser extent. The proportion of the beam which is reflected is influenced by this. The portion of the beam which is reflected is measured.

Normally this measurement is corrupted by various interference factors, and while a reduction in interference can be achieved by pulse synchronization of the transmitter and receiver, interference factors are still considerable, particularly daylight interference in the visible light range. This means that it is difficult to make an exact and reliable measurement.

Therefore, the invention provides at least two filters 4 which are shown in FIG. 1 in an abstract form, the effect of the filters is shown in the relevant filter graphs.

The upper filter graph in FIG. 1 shows the narrow-band emitted beam as the operational range. Filter 4, in the form of a layer on the beam exit surface applied, for example, by vacuum evaporation, is a band pass filter, whose pass range is shown in curve 4'. The upper edge of the pass range corresponds to the upper edge of the operational range.

The lower edge is not shown in the graph and is not mentioned specifically in the following text. Beam guide 1 is used as a second filter. Additives to the material of the beam guide which are optically active render the beam guide a band pass filter with the pass range shown in curve 1'. The lower edge of the pass range of curve 1' is approximately the same as the lower edge of the operational range. The pass curves have an area of overlap which basically corresponds with the operational range. Because of this configuration, the beam of rays which exits from the beam guide is limited to a great extent to the operational range. Radiation outside the operational range is filtered out. It is particularly advantageous if the pass range is in the region of approximately 650 to 750 microns.

In the lower curve shown in FIG. 1 filter 4 is in the form of an interference filter exhibiting filter curve 4". The remaining configuration is the same. Here also the beam of rays which exits from the beam guide is limited to the operational range.

Figure 2:
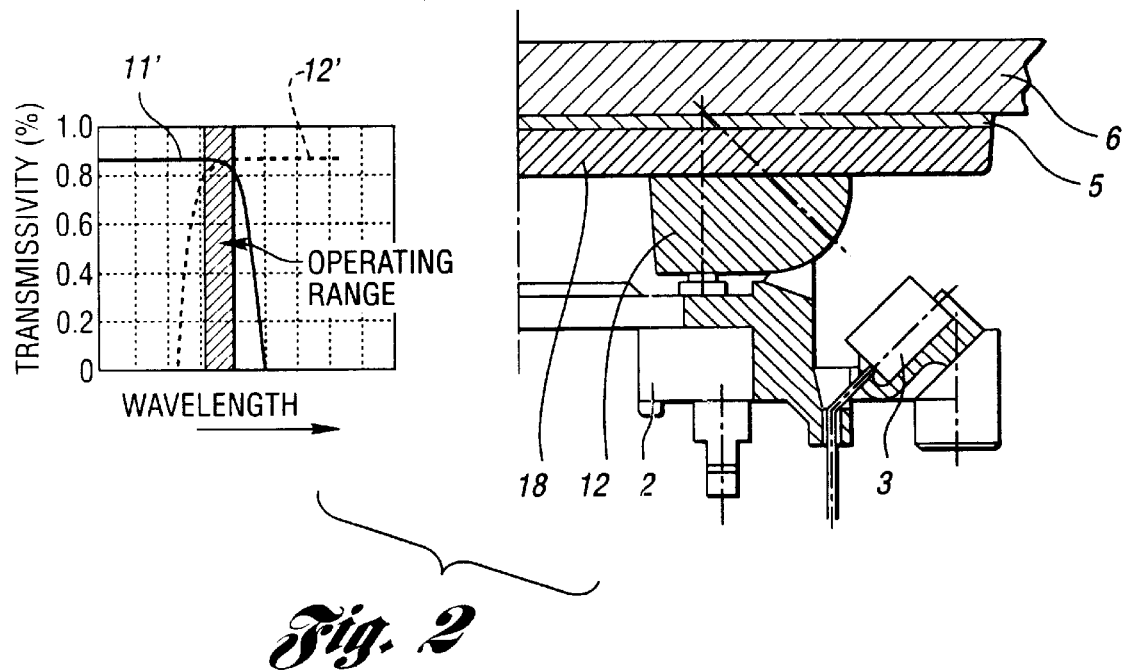
FIG. 2 is a section and one filter diagram for a further design example.

In the example shown in FIG. 2, beam guide 1 on the one hand and support piece 12 with the convergent lens on the other hand are in the form of two separate components. Through the addition of optically active components to the beam guide material, beam guide 1 functions as a band pass filter with the pass curve 1'. Support piece 12 also functions as a band pass filter with the pass curve 12'.

Figure 3:
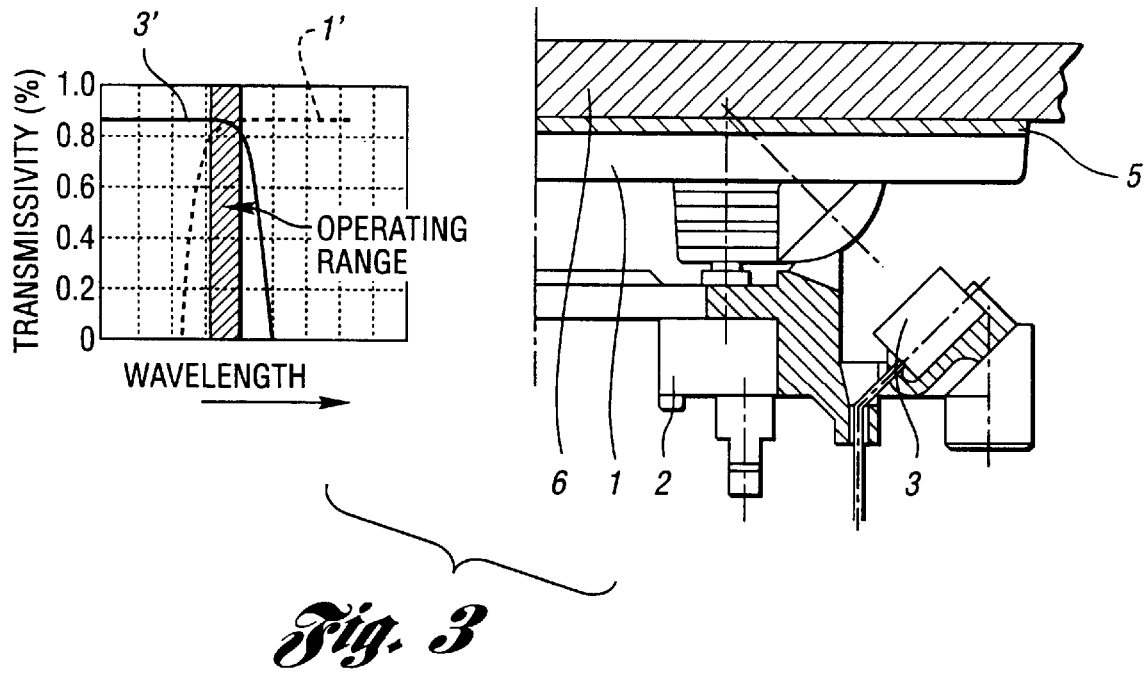
FIGS. 3 to 7 correspond to illustrations of further design examples.

In the case of the example shown in FIG. 3, beam guide 1 and receiver 3 are each in the form of band pass filters. The corresponding filter curves 1' and 3' are illustrated in the diagram. In each case, one edge of the pass range lies on one side of the operational range so that the overlapping area corresponds with the operational area.

Figure 4:
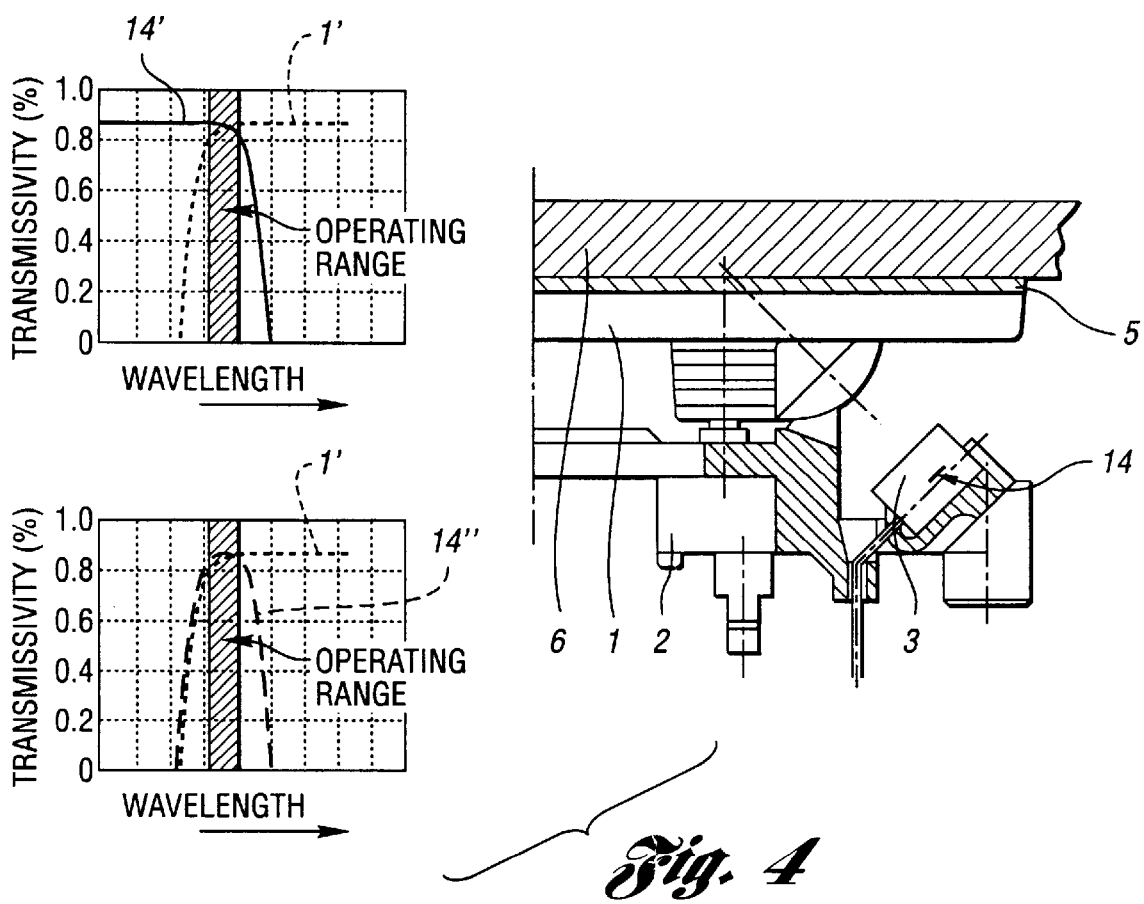

In the design example shown in FIG. 4, the beam guide 1 is in the form of a band pass filter with the filter curve 1'. A further filter 14 is combined with receiver 3 and is in the form of a band pass filter with curve 14' or in the form of an interference filter with filter curve 14".

Figure 5:
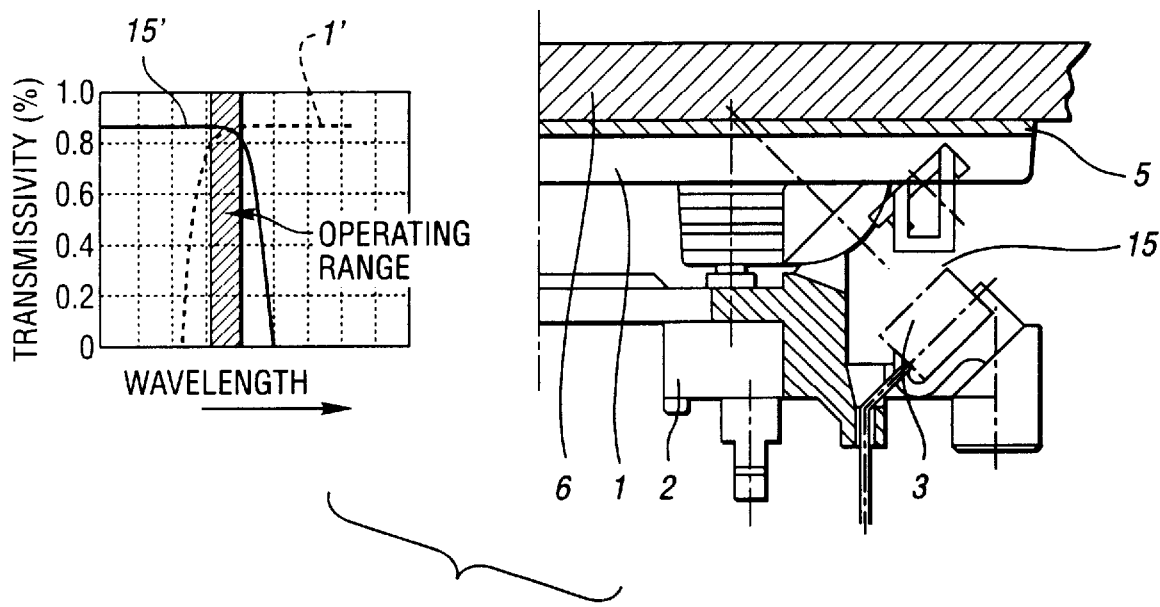

In the example shown in FIG. 5, the beam guide 1 is designed as a band pass filter with filter curve 1'. A filter 15 with filter curve 15' is mounted in the vicinity of receiver 3.

Figure 6:
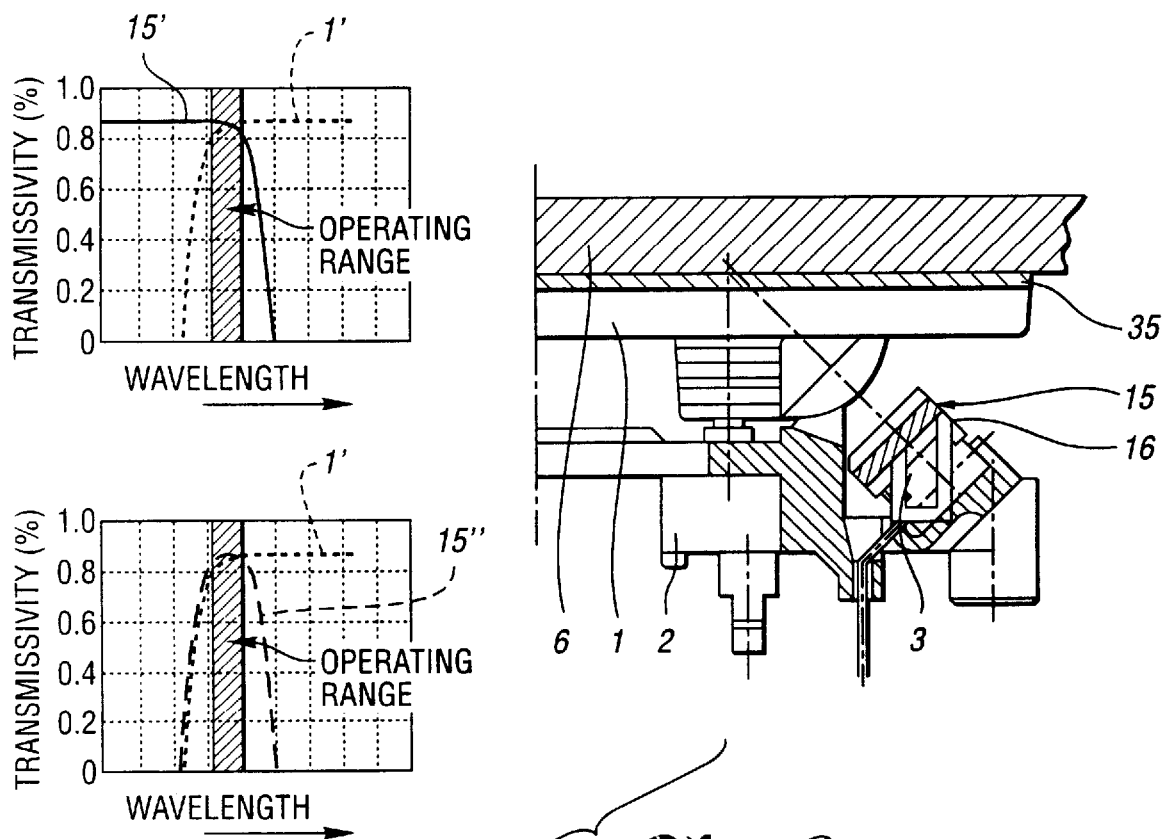

In the example shown in FIG. 6 beam guide 1 is likewise in the form of a band pass filter with filter curve 1'. A further filter 15 is present on holder 16 which carries receiver 3. Filter 15 can be in the form of a band pass filter with filter curve 15' or in the form of an interference filter with filter curve 15".

Figure 7:
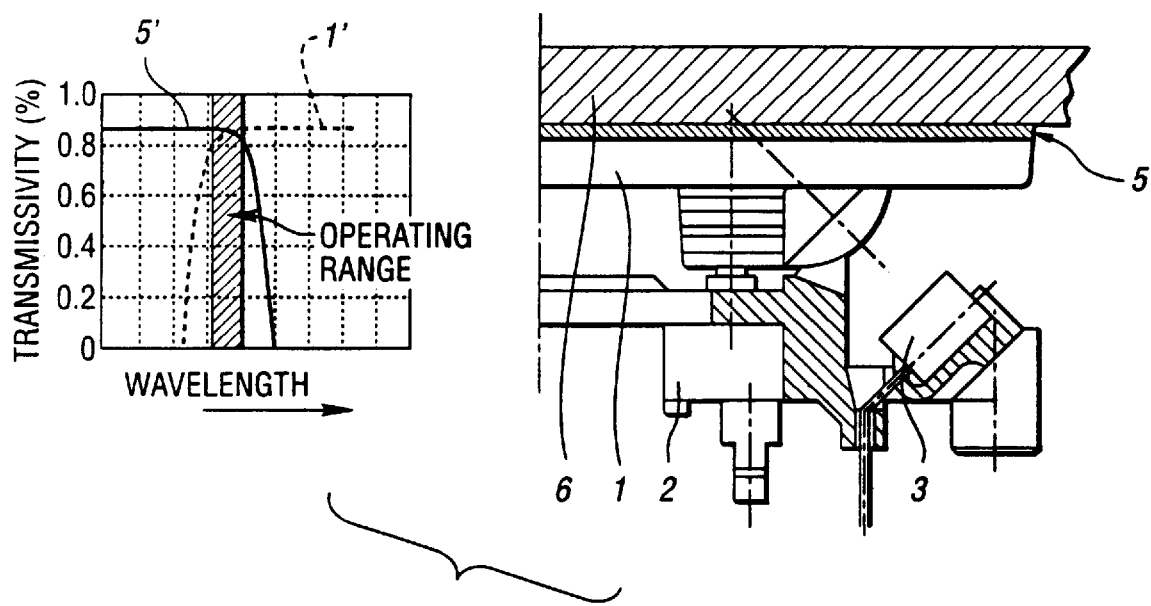

In the example shown in FIG. 7, beam guide 1 and coupling medium 5 are in the form of band pass filters, with the curves 1' and 5' respectively.

Based on these examples other filter combinations are possible which would be obvious to one versed in the art, and these also will fall within the scope of this patent.

What is claimed is:

1. An optoelectronic sensor for detecting wetness on a transparent windshield, the sensor comprising:

a beam guide having first and second parallel boundary surfaces, an entrance coupling surface, and an exit coupling surface, the coupling surfaces positioned at opposite ends of the beam guide and slanted relative to the beam guide, the first boundary surface cooperating by way of an optical coupling medium with the windshield and the second coupling surface cooperating with the entrance and exit coupling surfaces;

an optical transmitter having a narrow band operating range optically coupled to the entrance coupling surface, the transmitter defining a first end of an optical beam path;

an optical receiver having a narrow band operating range optically coupled to the exit coupling surface, the receiver defining a second end of the optical beam path;

a first filter incorporated into the beam path having an associated first pass range; and a second filter incorporated into the beam path having an associated second pass range, wherein the first and second pass ranges overlap within the narrow band operating range of the transmitter and the receiver.

2. The sensor of claim 1 wherein the operating range is within the spectral region of about 650 $\mu$m to 750 $\mu$m.

3. The sensor of claim 2 wherein at least one of the first and second filters comprises an interference filter having a pass range substantially corresponding to the narrow band operating range.

4. The sensor of claim 1 wherein at least one of the first and second filters comprises an interference filter having a pass range substantially corresponding to the narrow band operating range.

5. The sensor of claim 4 wherein at least one of the first and second filters comprises a band pass filter having a pass band which includes the narrow band operating range, the pass band having at least one band edge near an edge of the narrow band operating range.

6. The sensor of claim 1 wherein at least one of the first and second filters comprises a band pass filter having a pass band which includes the narrow band operating range, the pass band having at least one band edge near an edge of the narrow band operating range.

7. The sensor of claim 6 wherein the first filter comprises a low pass filter and the second filter comprises a high pass filter, the first and second filters overlapping in the narrow band operating range.

8. The sensor of claim 7 wherein the first and second filters are positioned at opposite ends of the beam path.

9. The sensor of claim 1 wherein at least one of the first and second filters comprises the beam guide.

10. The sensor of claim 9 wherein the beam guide comprises a mixture of glass materials selected to produce the pass range.

11. The sensor of claim 1 wherein at least one of the first and second filters comprises a dielectric layer applied to the beam guide by sputtering.

12. The sensor of claim 1 wherein at least one of the first and second filters is integrally formed within the optical coupling medium.

13. The sensor of claim 12 wherein the optical coupling medium comprises an adhesive layer.

14. The sensor of claim 1 further comprising a receiver carrier which cooperates with the optical receiver wherein the second filter comprises an additional element on the receiver carrier.

15. An optoelectronic sensor for detecting wetness on a transparent windshield, the sensor comprising:

a beam guide having first and second parallel boundary surfaces, an entrance coupling surface, and an exit coupling surface, the coupling surfaces positioned at opposite ends of the beam guide and slanted relative to the beam guide, the first boundary surface cooperating by way of an optical coupling medium with the windshield and the second coupling surface cooperating with the entrance and exit coupling surfaces, the beam guide also having an associated optical first pass range;

an optical transmitter having a narrow band operating range optically coupled to the entrance coupling surface, the transmitter defining a first end of an optical beam path;

an optical receiver having a narrow band operating range optically coupled to the exit coupling surface, the receiver defining a second end of the optical beam path;

a filter incorporated into the optical beam path having an associated second pass range wherein the second pass range overlaps with the first pass range within the narrow band operating range of the transmitter and the receiver.

* * * * *